(12) United States Patent
Glad et al.

(10) Patent No.: US 8,685,248 B2
(45) Date of Patent: Apr. 1, 2014

(54) PURIFICATION OF IMMUNOGLOBULINS

(75) Inventors: Gunnar Glad, Uppsala (SE);
Bo-Lennart Johansson, Uppsala (SE);
Jean-Luc Maloisel, Uppsala (SE); Nils Norrman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1075 days.

(21) Appl. No.: 12/709,556

(22) Filed: Feb. 22, 2010

(65) Prior Publication Data
US 2010/0151581 A1 Jun. 17, 2010

Related U.S. Application Data

(62) Division of application No. 10/584,714, filed as application No. PCT/SE2004/002007 on Dec. 21, 2004, now abandoned.

(30) Foreign Application Priority Data

Dec. 23, 2003 (SE) ...................................... 0303532

(51) Int. Cl.
*B01D 15/08* (2006.01)
(52) U.S. Cl.
USPC ..... 210/635; 210/656; 210/198.2; 210/502.1; 530/387.1; 530/413; 530/417
(58) Field of Classification Search
USPC ......... 210/635, 656, 198.2, 502.1; 530/387.1, 530/413, 417
See application file for complete search history.

(56) References Cited

U.S. PATENT DOCUMENTS

| 4,212,905 | A | 7/1980 | Tsibris |
| 4,725,355 | A | 2/1988 | Yamamoto et al. |
| 4,752,398 | A | 6/1988 | Holbein et al. |
| 5,043,062 | A | 8/1991 | Bale et al. |
| 5,203,991 | A | 4/1993 | Kutsuna et al. |
| 5,240,602 | A | 8/1993 | Hammen |
| 5,453,186 | A | 9/1995 | Muller et al. |
| 6,090,288 | A | 7/2000 | Berglund et al. |
| 6,117,996 | A | 9/2000 | Lowe et al. |
| 6,498,236 | B1 | 12/2002 | Lihme et al. |
| 7,060,187 | B2 | 6/2006 | Ihre et al. |
| 2005/0065282 | A1 | 3/2005 | Ihre et al. |
| 2008/0299671 | A1* | 12/2008 | Glad et al. .................. 436/161 |

FOREIGN PATENT DOCUMENTS

EP 0 197 521 10/1986

OTHER PUBLICATIONS

Database WPI Week 198715, Derwent Publications Ltd., London, GB; AN 1987-105706 & JP 62 053669 A (Terumo Corp), Mar. 9, 1987 abstract.
Database WPI Week 198808, Derwent Publications Ltd., London GB; AN 1988-053325 & JP 63 009450 A (Terumo Corp), Jan. 16, 1988 abstract.

(Continued)

*Primary Examiner* — Ernest G Therkorn

(57) ABSTRACT

The present invention relates to a separation matrix comprised of a porous support to which ligands have been immobilized, wherein said ligands comprise at least one aliphatic sulphonamide. The nitrogen of the sulphonamide may be a secondary or tertiary amine. The invention also relates to a chromatography column that contains the described separation matrix, as well as to a method of isolating immunoglobulin-like compounds by adsorption to a separation matrix that comprises aliphatic sulphonamide ligands.

10 Claims, 1 Drawing Sheet

Cysteamine

Ammonia

Diethylenetriamine

Triethylenetetramine

(56) References Cited

OTHER PUBLICATIONS

Arshady, R., "Styrene Based Polymer Supports Developed by Suspension Polymerization", La Chimica E L' Industria, vol. 70, No. 9, 1988, p. 70-75.

Hjerten, S., "The Preparation of Agarose Spheres for Chromatography of Molecules and Particles", Biochimica ET Biophysica Acta, vol. 79, 1964, p. 393-398.

Knudsen, K., et al., "Sulfone-Aromatic Ligands for Thiophilic Adsorption Chromatography: Purification of Human and Mouse Immunoglobulins", Analytical Biochemistry, vol. 201, 1992, p. 170-177.

Liu, Y., et al., "Novel Sulfamethazine Ligand used for One-Step Purification of Immunoglobulin G from Human Plasma", Journal of Chromatography B, vol. 792, 2003, p. 177-185.

Porath, J., et al., "Thiophilic Adsorption—A New Method for Protein Fractionation", FEBS, vol. 185, No. 2, 1985, p. 306-310.

Porath, J., et al., "A New Kind of "Thiophilic" Electron-Donor-Acceptor Adsorbent", Makromol Chem., Macromol. Symp., vol. 17, 1988, p. 359-371.

Schwarz, A., et al., "Novel Herterocyclic Ligands for the Thiophilic Purification of Antibodies", Journal of Chromatography B, vol. 664, 1995, p. 83-88.

Introduction to Organic Chemistry, Streitwieser A. and Heathcock C. H., MacMillan Publishing Co., 1976, pp. 789-790.

Wikipedia, Sulfonamide, undated.

\* cited by examiner

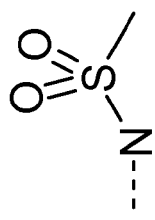
Ammonia
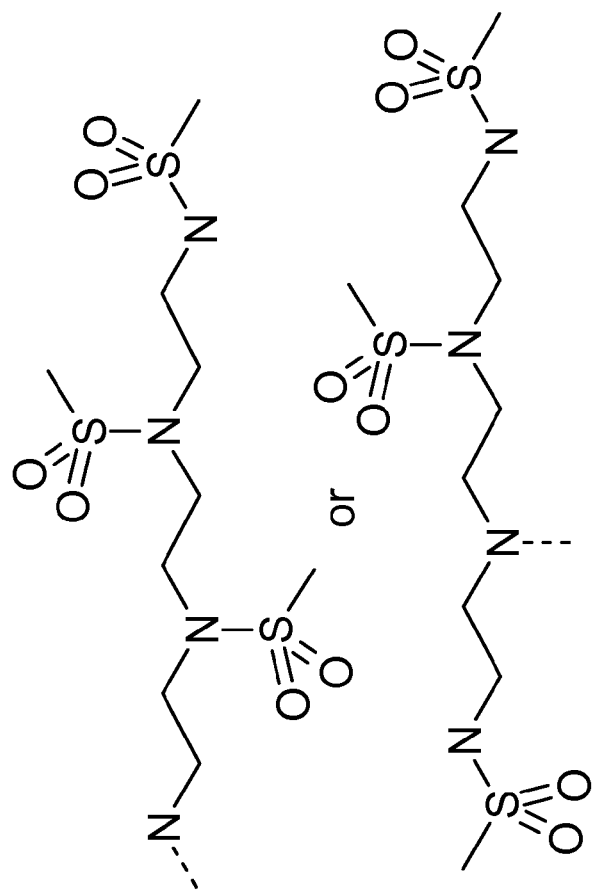
Triethylenetetramine
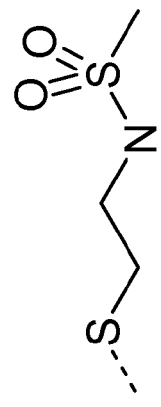
Cysteamine
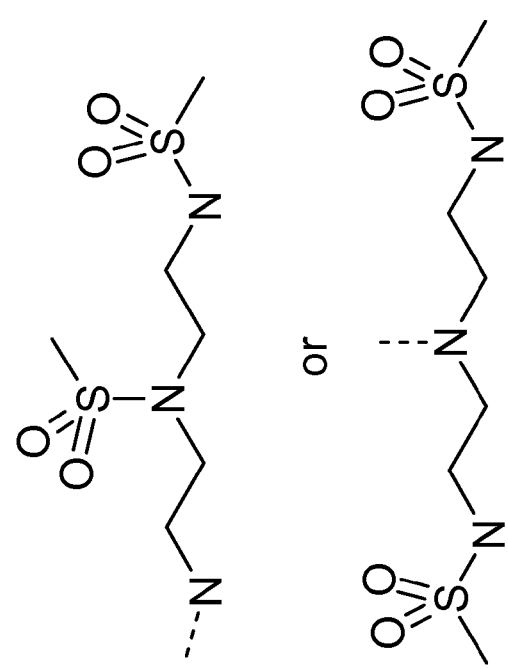
Diethylenetriamine

PURIFICATION OF IMMUNOGLOBULINS

CROSS-REFERENCE TO RELATED APPLICATIONS

This application is divisional of U.S. patent application Ser. No. 10/584,714 filed Jun. 23, 2006, now abandoned, which is a filing under 35 U.S.C. §371 and claims priority to international patent application number PCT/SE2004/002007 filed Dec. 21, 2004, published on Jul. 7, 2005, as WO 2005/061543, which claims priority to application number 0303532-6 filed in Sweden on Dec. 23, 2003.

FIELD OF THE INVENTION

The present invention relates to the field of antibody preparation, and more specifically to a separation matrix for isolation of antibodies. The invention also encompasses a chromatography column that comprises the novel matrix and a method of isolating antibodies.

BACKGROUND OF THE INVENTION

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. Five different classes of antibodies, or immunoglobulins, exist: IgA, IgD, IgE, IgG, and IgM. They differ not only in their physiological roles but also in their structures. From a structural point of view, IgG antibodies are a particular class of immunoglobulins that have been extensively studied, perhaps because of the dominant role they play in a mature immune response.

The biological activity, which the immunoglobulins possess, is today exploited in a range of different applications in the human and veterinary diagnostic, health care and therapeutic sector. In fact, in the last few years, monoclonal antibodies and recombinant antibody constructs have become the largest class of proteins currently investigated in clinical trials and receiving FDA approval as therapeutics and diagnostics. Complementary to expression systems and production strategies, purification protocols are designed to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents being ethanol, polyethylene glycol, lyotropic i.e. anti-chaotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

Ion exchange chromatography is another well-known method of protein fractionation frequently used for isolation of immunoglobulins. However, since the charged ion exchange ligands will react with all oppositely charged compounds, the selectivity of ion exchange chromatography may be somewhat lower than other chromatographic separations.

Protein A and Protein G affinity chromatography are popular and widespread methods for isolation and purification of immunoglobulins, particularly for isolation of monoclonal antibodies, mainly due to the ease of use and the high purity obtained. Used in combination with ion exchange, hydrophobic interaction, hydroxyapatite and/or gel filtration steps, especially protein A-based methods have become the antibody purification method of choice for many biopharmaceutical companies. However, despite their common usage, there is a growing need and demand for effective alternatives addressing familiar problems associated with protein A-based media, such as cost, leakage and instability at increased pH values.

Hydrophobic interaction chromatography (HIC) is also a method widely described for isolation of immunoglobulins. However, hydrophobic matrices require an addition of lyotropic salts to the raw material to make the immunoglobulin bind efficiently. The bound antibody is released from the matrix by lowering the concentration of lyotropic salt in a continuous or stepwise gradient. If a highly pure product is the object, it is recommended to combine the hydrophobic chromatography with a further step. Thus, a disadvantage of this procedure is the necessity to add lyotropic salt to the raw material as this gives a d problem and thereby increased cost to the large-scale user. For other raw materials than cell culture supernatants such as whey, plasma, and egg yolk the addition of lyotropic salts to the raw materials would in many instances be prohibitive in large-scale applications as the salt could prevent any economically feasible use of the immunoglobulin depleted raw material. An additional problem in large-scale applications would be the disposal of several thousand liters of waste.

Thiophilic adsorption chromatography was introduced by J. Porath in 1985 (J. Porath et al; FEBS Letters, vol. 185, p. 306, 1985) as a new chromatographic adsorption principle for isolation of immunoglobulins. In this paper, it is described how divinyl sulphone activated agarose coupled with various ligands comprising a free mercapto-group show specific binding of immunoglobulins in the presence of 0.5 M potassium sulphate, i.e. a lyotropic salt. It was postulated that the sulphone group, from the vinyl sulphone spacer, and the resulting thioether in the ligand was a structural necessity to obtain the described specificity and capacity for binding of antibodies. It was however later shown that the thioether could be replaced by nitrogen or oxygen if the ligand further comprised an aromatic radical (K. L. Knudsen et al, Analytical Biochemistry, vol. 201, p. 170, 1992). Although the matrices described for thiophilic chromatography generally show good performance, they also have a major disadvantage in that it is needed to add lyotropic salts to the raw material to ensure efficient binding of the immunoglobulin, which is a problem for the reasons discussed above.

Other thiophilic ligands coupled to epoxy activated agarose have been disclosed in (J. Porath et. al. Makromol. Chem., Makromol. Symp., vol. 17, p. 359, 1988) and (A. Schwarz et. al., Journal of Chromatography B, vol. 664, pp. 83-88, 1995), e.g. 2-mercaptopyridine, 2-mercaptopyrimidine, and 2-mercaptothiazoline. However, all these affinity matrices still have inadequate affinity constants to ensure an efficient binding of the antibody without added lyotropic salts.

U.S. Pat. No. 6,498,236 (Upfront Chromatography) relates to isolation of immunoglobulins. The method disclosed involves the steps of contacting a solution that comprises a negatively charged detergent and contains immunoglobulin(s) with a solid phase matrix, whereby at least a part of the immunoglobulins becomes bound to the solid phase matrix; and contacting the solid phase matrix with an eluent in order to liberate the immunoglobulin(s) from the solid phase matrix. The immunoglobulin-containing solution is further characterised by having a pH in the range of 2.0 to 10.0, a total salt content corresponding to an ionic strength of at the most 2.0, and lyotropic salts in a concentration of at the most 0.4 M. The detergent present in the solution is believed to suppress the adherence of other biomolecules to the matrix, and may be exemplified by octyl sulphate, bromphenol blue, octane sulphonate, sodium laurylsarcosinate, and hexane sulphonate. The solid phase matrix is defined by the formula M-SP1-L, wherein M designates the matrix backbone, SP1 designates a ligand comprising a mono- or bicyclic aromatic or heteroaromatic moiety.

Liu et al (Yang Liu, Rui Zhao, Dihua Shangguan, Hongwu Zhang, Guoquan Liu: Novel sulfinethazine ligand used for one-step purification of immunoglobulin G from human plasma, Journal of Chromatography B, 792 (2003) 177-185) investigated the affinity of sulfinethazin (SMZ) to human IgG. Thus, a ligand is disclosed, which comprises a sulphonyl group wherein the R group is a heterocyclic ring. According to this article, SMZ was immobilised on monodisperse, non-porous, cross-linked poly(glycidyl methacrylate) beads. The beads were then used in high-performance affinity chromatography for isolation of IgG from human plasma. Maximal adsorption was achieved at pH 5.5. The beads presented minimal non-specific interaction with other proteins. Thus, the ligands were capable of adsorbing antibodies, while their interaction with other proteins was just sufficient to provide retardation thereof in the adsorption buffer used. However, as is well known, ester compounds such as methacrylate are easily hydrolysed at increased pH values. Consequently, similar to Protein A and Protein G matrices, the therein disclosed separation matrix would be expected to unstable at the commonly used cleaning in place (cip) procedures.

U.S. Pat. No. 4,725,355 relates to a body fluid purification medium comprising a support and an adsorbent, which includes at least one sulfa drug, for adsorbing and removing a pathogenic substance in a body fluid. The sulfa drug is a chemotherapeutic agent, and more specifically a sulfonamide characterised by aromatic R group(s). The medium can be provided in a body fluid flow path provided in a container between body fluid inlet and outlet ports.

EP 0 197 521 relates to an immunoglobulin adsorbent and an adsorption apparatus. More specifically, an adsorbent for immunoglobulin is disclosed, which adsorbent comprises a hydroxyl-containing water-insoluble carrier to which a diamine compound has been attached. The diamine compound is represented by the general formula:

NH$_2$(CH$_2$)$_n$NH$_2$ wherein n is an integer having a value of 3 to 9. The compound has been attached through a silane coupling agent or a derivative thereof, with a heterocyclic compound being attached to the diamine through a difunctional reagent. Thus, the R groups are aromatic structures.

However, there is still a need of alternative methods for purification of antibodies or antibody constructs, which observe the demands of purity, safety, potency and cost effectiveness.

SUMMARY OF THE INVENTION

Accordingly, one aspect of the present invention is a separation matrix, which enables adsorption of antibodies at low ionic strengths at pH values around neutral. This can be achieved by the separation matrix as defined in claim 1.

Another aspect of the present invention is a separation matrix, which enables highly selective adsorption of antibodies.

A specific aspect of the present invention is a separation matrix to which antibodies are adsorbed, while other proteins are allowed to pass without any essential interaction.

A further aspect of the present invention is to a process of preparing a matrix for separation of antibodies, which comprises functional groups that enable adsorption of antibodies by thiophilic, hydrophobic and/or hydrogen bond interactions, which method makes it easy to vary the ligand structure. This can be achieved by immobilisation of amines and/or polyamines to a porous support and a subsequent step of sulphonylating said immobilised amines.

Yet another aspect of the invention is to a method of isolating antibodies from a liquid by adsorption thereof to a separation matrix, which method does not require any addition of detergent to achieve adsorption.

Further aspects and advantages of the invention will appear from the detailed description that follows.

BRIEF DESCRIPTION OF THE DRAWINGS

FIG. 1 shows some selected examples of sulphonylated amines with potential attachment points to a support. More specifically, FIG. 1 shows, from left to right cysteamine; ammonia (upper line); and diethylenetriamine; and triethylenetetramine (lower line).

DEFINITIONS

The terms "antibody" and "immunoglobulin" are used herein interchangeably.

The term "ligand" means herein molecules or compounds capable of interaction with target compounds, such as antibodies.

The term "spacer arm" means herein an element that distances a ligand from the support of a separation matrix.

A "primary amine" is defined by formula RNH$_2$, wherein R denotes an organic group.

A "secondary amine" is defined by formula R$_2$NH, wherein R denotes an organic group.

The term "sulphonamide" is used in its conventional meaning i.e. for any chemical compound, that comprises one or more amides of sulfonic acids.

A sulphonyl group is defined by formula S($=$O)$_2$R, wherein R denotes an organic group.

The term "eluent" is used in its conventional meaning in this field, i.e. a buffer of suitable pH and/or ionic strength to release one or more compounds from a separation matrix.

DETAILED DESCRIPTION OF THE INVENTION

In a first aspect, the present invention is a separation matrix comprised of a porous support to which ligands have been immobilised, optionally via spacer arms, wherein said ligands comprise one or more sulphonamides wherein at least one R group of the sulphonyl is an aliphatic compound.

In one embodiment, the sulphonamide is coupled to the porous support via its nitrogen. In an alternative embodiment, the sulphonamide is coupled to the porous support via its sulphur. However, the present invention also encompasses separation matrices which are comprised of sulphonamides that are coupled in different directions, i.e. ligands that are a mixture of amide-coupled and sulphone-coupled sulphonamides.

In one embodiment, said ligands comprise at least one primary or secondary amine.

The separation matrix can be used for isolation, such as purification or analysis, of antibodies and other compounds that exhibit equivalent binding properties, such as fusion proteins comprising an immunoglobulin part or antibody fragments. The present inventors have shown that antibodies can be purified at a high capacity and with an excellent selectivity using a separation matrix that comprises one or more sulphonamides. Contrary to the above discussed U.S. Pat. No. 6,498,236, which utilises aromatic or heteroaromatic moieties as ion exchange ligands for antibody purification, the present invention achieves purification without any need of adding detergent to the liquid that comprises antibodies before its contact with the matrix using uncharged ligands.

As is well known, a sulphonamide is comprised of an amine, wherein at least one of the R groups of said amine is a sulphonyl group. In one embodiment of the present matrix, the R group of the sulphonyl is an aliphatic acyclic or cyclic group, such as a linear chain of 1-4, such as 1 or 2, carbons and/or heteroatoms from which one or more hydrogens may have been substituted with heteroatoms. In one embodiment, the aliphatic R group of the sulphonyl is a methyl group. In an alternative embodiment, the aliphatic R group of the sulphonyl is an ethyl group.

In an alternative embodiment, the R group of the sulphonyl is a substituted or unsubstituted aromatic group, such as a mono- or polyaromatic group. In yet another embodiment, the R group of the sulphonyl comprises both aliphatic and aromatic groups.

In one embodiment of the present separation matrix, the ligands are sulphonylated monoamines, such as cysteamine or ammonia. In an alternative embodiment, the ligands are sulphonylated polyamines, such as trietylentetraamine. Such sulphonylated polyamines may comprise any convenient number of amines, such as 2-10. In an illustrative embodiment, each polyamine comprises two to six amines.

In a specific embodiment of the present separation matrix, the ligands are present as repetitive units of a polymer immobilised to the support. The polymer may be any suitable polyamine, such as polyalkyleneimine. In one embodiment, the polymer is a polyethylene amine. As the skilled person in this field will realise, the amine content of such a polymer may be varied, e.g. to comprise primary and/or secondary amines in any desired order. Thus, in one embodiment, the polymer exhibit two or more different ligand groups. The polymers are easily produced from suitable monomers according standard methods in this field. Methods of coupling the polyamines to a support are also well known and easily performed by the skilled person in this field, for example by in situ polymerisation or grafting of polymers, see e.g. U.S. Pat. No. 7,060,187 (Ihre et al). An advantage of this embodiment is that it enables convenient optimisation of the properties of the separation matrix, e.g. by variation of the polymer length, branching etc.

In one embodiment, the ligands are acyclic compounds.

The porous support of the present separation matrix may be of any suitable material. In one embodiment, the support is comprised of a cross-linked carbohydrate material, such as agarose, agar, cellulose, dextran, chitosan, konjac, carrageenan, gellan, alginate etc. The support can easily be prepared according to standard methods, such as inverse suspension gelation (S Hjertén: Biochim Biophys Acta 79(2), 393-398 (1964). Alternatively, the support is a commercially available product, such as SEPHAROSE™ FF (GE Healthcare Bio-Sciences AB, Uppsala, Sweden). Thus, in one embodiment of the present matrix, the support is a cross-linked polysaccharide. In a specific embodiment, said polysaccharide is agarose. Such carbohydrate materials are commonly allylated before immobilisation of ligands thereof. In brief, allylation can be carried out with allyl glycidyl ether, allyl bromide or any other suitable activation agent following standard methods.

In an alternative embodiment, the porous support of the present separation matrix is comprised of cross-linked synthetic polymers, such as styrene or styrene derivatives, divinylbenzene, acrylamides, acrylate esters, methacrylate esters, vinyl esters, vinyl amides etc. Supports of such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare Bio-Sciences AB, Uppsala, Sweden) can be surface-modified according to the invention. However, in this embodiment, the surface of the support is preferably modified to increase its hydrophilicity, usually be converting the majority of the exposed residual double bonds to hydroxyl groups.

The present separation matrix in any suitable form, such as a chromatography matrix, e.g. in the form of essentially spherical particles or a monolith; a filter or membrane; a chip, a surface, capillaries or the like. Thus, the present invention also encompasses a chromatography column packed with a separation matrix as described above. In an advantageous embodiment, the column is made from any conventional material, such as a biocompatible plastic, e.g. polypropylene, or glass. The column may be of a size suitable for laboratory scale or large-scale purification of antibodies. In a specific embodiment, the column according to the invention is provided with luer adaptors, tubing connectors, and domed nuts. Thus, the present invention also encompasses a kit comprised of a chromatography column packed with a separation matrix as described above; at least one buffer; and written instructions for purification of antibodies in separate compartments. In a specific embodiment, the present kit also comprises luer adaptors, tubing connectors, and domed nuts.

In a second aspect, the present invention relates to a process of preparing a matrix for separation of antibodies, which method comprises a first step of immobilising amines and/or polyamines to a porous support and a subsequent step of sulphonylating said amines. The porous support may be as described above, and any standard methods for immobilisation may be used, see e.g. Immobilized Affinity Ligand Techniques, Hermanson et al, Greg T. Hermanson, A. Krishna Mallia and Paul K. Smith, Academic Press, Inc., 1992. However, as the skilled person in this field will realise, some of the separation matrices may equally well be prepared by immobilisation of sulphonamides directly to the support, depending on the nature of the ligand.

In a third aspect, the present invention is a method of isolating antibodies from a liquid, which method comprises the steps of (a) providing a liquid that comprises at least one antibody:

(b) contacting said liquid with a separation matrix comprising one or more sulphonamide groups, whereby one or more antibodies are adsorbed to said matrix; and, optionally, (c) passing an eluent over said matrix to release one or more antibodies; and (d) recovering at least one antibody from a fraction of the eluent.

In this context, it is to be understood that the term "antibodies" also includes antibody fragments and any fusion protein that comprises an antibody or an antibody fragment. Thus, the present method is useful to isolate any immunoglobulin-like molecule, which presents the binding properties of an antibody. The liquid comprising an antibody may for example be a liquid originating from a cell culture producing antibodies or a fermentation broth, from which it is desired to purify one or more desired antibodies. Alternatively, the liquid may be blood or blood plasma, from which it is desired to remove one or more antibodies to obtain a liquid which is pure in that respect. Thus, in one embodiment of the present method, the liquid provided in step (a) also comprises one or more other proteins than antibodies. As will be shown in the experimental part below, in general, the present method allows selective adsorption of antibodies at relatively low ionic strengths. Unexpectedly, the present inventors found that the use of a porous separation matrix that exhibits one or more sulphonamide groups enables the adsorption of antibodies while other proteins than antibodies are not adsorbed. Accordingly, the present method provides pure preparations of antibodies in high yields. The skilled person in this field can easily select the optimal conditions for each sulphonamide ligand structure using routine experimentation, as will be discussed in the experimental part below. For example, it is well known in this field that properties of a separation matrix can be optimised by variation of either the nature of the gel; in this case, the R group of the sulphonamide, or the degree of substitution i.e. the ligand density on the support. The salt concentration in the adsorption buffer can also be optimised for each ligand. Thus, in one embodiment of the present invention, the adsorption of step (b) is provided at a salt concentration of about 0.25 M $Na_2SO_4$. In a specific embodiment, the ligands comprise monoamines, and step (b) is performed at a salt concentration above about 0.5 M $Na_2SO_4$.

The present method can use a separation matrix in any suitable form, such as a chromatography matrix, e.g. in the form of essentially spherical particles or a monolith; a filter or membrane; a chip or the like. Thus, in an advantageous embodiment, the separation matrix of step (b) is provided in a chromatography column.

The support and the ligands of the separation matrix of step (b) may be anyone of the ones described above.

As mentioned above, the present invention has unexpectedly shown that using the novel separation matrix according to the invention enables highly selective adsorption of antibodies at a neutral pH. Thus, in one embodiment, step (b) is performed at a pH of 6.5-8.3, such as 7.2-7.6, e.g. about 7.4.

The antibodies adsorbed to the column are easily released by standard elution such as by use of an eluent of decreasing ionic strength. Thus, in one embodiment, step (c) is a gradient elution performed by adding an eluent of decreasing salt concentration to the separation matrix, preferably by passing said eluent over the matrix. The gradient may be of any shape, such as a linear or stepwise gradient. Other elution schemes are also useful, such as adding a competitive binder in the eluent, adding to the eluent a compound that displaces the adsorbed antibodies on the matrix, such as an alcohol, a salt etc, or providing a temperature change etc.

Alternatively, the elution of step (c) is performed by an adjustment of the pH, such as a decrease or increase of pH. A pH adjustment can also be combined with a salt gradient, as discussed above. In a specific embodiment, step (b) is performed at a pH above neutral, and step (c) is a gradient elution performed by adding an eluent of decreasing pH.

The present method is useful to recover any kind of monoclonal or polyclonal antibody, such as antibodies originating from mammalian hosts, such as mice, rodents, primates and humans, or antibodies originating from cultured cells such as hybridomas. In one embodiment, the antibodies recovered in step (d) are human or humanised antibodies. The antibodies may be of any class, i.e. selected from the group that consists of IgA, IgD, IgE, IgG, and IgM. In a specific embodiment, the antibodies recovered in step (d) are immunoglobulin G (IgG). The present invention also encompasses the purification of fragments of any one of the above mentioned antibodies as well as fusion proteins comprising such antibodies.

The present method allows quantitative adsorption of antibodies. Thus, in one embodiment, the present method encompasses a method as defined above and in addition a step (e) of determining the amount of antibody spectrophotometrically. Such methods and useful equipment are well known to the skilled person in this field. The present is also useful in analytical procedures.

Finally, the present invention also relates to a separation matrix comprised of a porous support to which ligands have been immobilised, optionally via spacer arms, wherein said ligands comprise one or more acetamide groups. Such acetamide groups may e.g. be triethylenetetramine. The support may be as described above in relation to the sulphonamide matrix. Immobilisation of acetamide groups to a porous support is easily performed by the skilled person in this field following standard methods, such as the ones referred to above. This aspect of the invention also encompasses a method of liquid chromatography using a separation matrix comprising acetamide ligands. Such a method is useful for separation of biomolecules, such as proteins, virus, nucleic acids, such as DNA or RNA, plasmids etc. Suitable conditions for adsorption and elution are easily selected by the skilled person in this field.

EXAMPLES

The present examples are provided for illustrative purposes only, and should not be construed as limiting the scope of the present invention as defined by the appended claims. All references given below and elsewhere in the present specification are hereby included herein by reference.

Example 1

Preparation of a Sulphonamide Separation Matrix

Provided below is the preparation of a separation matrix according to the invention, wherein the R group of the sulphonyl are aliphatic groups.

General:

Volumes of matrix refer to settled bed volume.

Weights of matrix given in gram refer to suction dry weight. It is understood that these matrices are still water solvated material.

For large scale reaction stirring is referring to a suspended, motor-driven stirrer since the use of magnet bar stirrer is prompt to damage the beads. Small-scale reactions (up to 20 ml or g of gel) were performed in closed vials and stirring refers to the use of a shaking table.

Conventional methods were used for the analysis of the functionality and the determination of the degree of allylation, epoxidation, or the degree of substitution of ion exchanger groups on the beads. These methods were eventually complemented by additional elementary analysis of the gels in particular for sulphur atom.

One way to prepare a separation matrix according to the invention is exemplified below, starting from a crosslinked agarose gel (SEPHAROSE™ 6 FF, GE Healthcare Bio-Sciences AB, Uppsala, Sweden). For each step, a specific example is described.

A. Introduction of Allyl Group on the Matrix

SEPHAROSE™ was activated with allyl glycidyl ether as follows: A 100 g quantity of SEPHAROSE™ 6 FF was suction dried to 78 g, mixed with 0.4 g of $NaBH_4$, 11 g of $Na_2SO_4$ and 60 ml of 50% aqueous solution of NaOH. The mixture was stirred for 1 hour at 50° C. After addition of 80 ml of allylglycidyl ether the suspension was left at 50° C. under vigorous stirring for an additional 20 hours. After filtration of the mixture, the gel was washed successively, with 500 ml distilled water, 500 ml ethanol, 200 ml distilled water 200 ml 0.2 M acetic acid and, 500 ml distilled water. Titration gave a degree of substitution of 0.4 mmol of allyl/ml of gel.

B. Introduction of Amines Groups on the Matrix

Apart from cysteamine, which immobilisation was performed under specific radical addition conditions, the amines groups were introduced on the matrix directly via the nitrogen atom of the amine groups. In a typical procedure, the coupling to the matrix was realised in preference via bromination of the allyl group and nucleophilic substitution under basic conditions.

Cysteamine SEPHAROSE™ (GE Healthcare Bio-Sciences AB, Uppsala, Sweden)

A 10 g quantity of allyl activated gel (0.4 mmol allyl groups/ml drained gel) was washed with dioxane and transferred to a reaction vessel containing a solution of cysteamine-HCl (1 g) in 12 ml dioxane. The reaction was heated to 70° C. and AIBN (0.9 g) was added. The reaction was left 17 hours under stirring at 70° C. After filtration of the reaction mixture, the gel was successively washed with 3×10 ml dioxane, 3×10 ml ethanol, 3×10 ml of distilled water, 3×10 ml aqueous 0.5 HCl and finally 3×10 ml of distilled water. Cysteamine SEPHAROSE™ gel was obtained with a degree of substitution 0.34 mmol amines/ml of gel.

Activation of Allyl SEPHAROSE™ Via Bromination

Bromine was added to a stirred suspension of 100 ml of allyl activated SEPHAROSE™ 6 FF (0.4 mmol allyl groups/ml drained gel), 4 g of AcONa and 100 ml of distilled water, until a persistent yellow colour was obtained. Sodium formate was then added till the suspension was fully decolourised. The reaction mixture was filtered and the gel washed with 500 ml of distilled water. The activated gel was then directly transferred to a reaction vessel and further reacted with the appropriate ligand.

Diethylenetriamine SEPHAROSE™

A 10 g quantity of bromine activated gel (0.4 mmol allyl groups/ml drained gel) was transferred to a reaction vial containing a solution of diethylenetriamine (12.5 ml). The reaction was left 17 hours under stirring at 50° C. After filtration of the reaction mixture the gel was successively washed with 3×10 ml of distilled water, 3×10 ml aqueous 0.5 HCl and finally 3×10 ml of distilled water. Diethylenetriamine SEPHAROSE™ gel was obtained with a degree of substitution 0.56 mmol amines/ml of gel.

Triethylenetetramine SEPHAROSE™

A 10 g quantity of bromine activated gel (0.4 mmol allyl groups/ml drained gel) was transferred to a reaction vial containing a solution of triethylenetetramine (12.5 ml). The reaction was left 17 hours under stirring at 50° C. After filtration of the reaction mixture, the gel was successively washed with 3×10 ml of distilled water, 3×10 ml aqueous 0.5 HCl and finally 3×10 ml of distilled water. Triethylenetetramine SEPHAROSE™ gel was obtained with a degree of substitution 0.62 mmol amines/ml of gel.

Pentaethylenehexamine SEPHAROSE™

A 10 g quantity of bromine activated gel (0.4 mmol allyl groups/ml drained gel) was transferred to a reaction vial containing a solution of pentaethylenehexamine (12.5 ml). The reaction was left 17 hours under stirring at 50° C. After filtration of the reaction mixture the gel was successively washed with 3×10 ml of distilled water, 3×10 ml aqueous 0.5 HCl and finally 3×10 ml of distilled water. Pentaethylenehexamine SEPHAROSE™ gel was obtained with a degree of substitution 0.61 mmol amines/ml of gel.

Polyethyleneimine SEPHAROSE™

A 10 g quantity of bromine activated gel (0.4 mmol allyl groups/ml drained gel) was transferred to a reaction vial containing a solution of 12.5 ml polyethyleneimine (50% in water). The reaction was left 17 hours under stirring at 50° C. After filtration of the reaction mixture the gel was successively washed with 3×10 ml of distilled water, 3×10 ml aqueous 0.5 HCl and finally 3×10 ml of distilled water. Polyethyleneimine SEPHAROSE™ gel was obtained with a degree of substitution 0.45 mmol amines/ml of gel.

Ammonia SEPHAROSE™

1) A 10 g quantity of bromine activated gel (0.32 mmol allyl groups/ml drained gel) was transferred to a reaction vial containing a solution of sodium azide (1 g) in water (3 ml) that has been adjusted to pH 12 by addition of a 50% aqueous solution of NaOH. The reaction was left 17 hours under stirring at 50° C. After filtration of the reaction mixture the gel was successively washed with 3×20 ml of distilled water and 3×10 ml DMF. The drained gel was further reduced in a solution of DTE (1.5 g) and DBU (1.2 ml) in DMF (7.5 ml), stirred for 18 h at room temperature. After filtration of the reaction mixture the gel was successively washed with 3×10 ml DMF, 3×10 ml ethanol and finally 3×10 ml of distilled water. Amine SEPHAROSE™ gel was obtained with a degree of substitution 0.21 mmol amine group/ml of gel.

2) A 10 g quantity of bromine activated gel (0.4 mmol allyl groups/ml drained gel) was transferred to a reaction vial containing a solution of sodium azide (1 g) in water (3 ml) that has been adjusted to pH 12 by addition of a 50% aqueous solution of NaOH. The reaction was left 17 hours under stirring at 50° C. After filtration of the reaction mixture the gel was successively washed with 3×20 ml of distilled water and 3×10 ml DMF. The drained gel was further reduced in a solution of DTE (1.5 g) and DBU (1.2 ml) in DMF (7.5 ml), stirred for 18 h at room temperature. After filtration of the reaction mixture the gel was successively washed with 3×10 ml DMF, 3×10 ml ethanol and finally 3×10 ml of distilled water. Amine SEPHAROSE™ gel was obtained with a degree of substitution 0.26 mmol amine group/ml of gel.

C. Derivatization with Sulphonyl Chloride

General Method

A 5 g quantity of amine coupled gel was washed with 3×10 ml ethanol followed by 3×10 ml DCM (dichloromethane). The gel was transferred to a vial and DCM (2 ml) and 3.3 equivalents of DIPEA were as well added, and the mixture stirred for 5 minutes. After dropwise addition of 3 equivalents of methylsulphonyl chloride dissolved in DCM (3 ml), the reaction mixture was stirred at room temperature for 18 h. After filtration of the reaction mixture the gel was successively washed with 3×10 ml DCM, 3×10 ml ethanol, 3×10 ml of distilled water, 3×10 ml 0.5M HCl and finally 3×10 ml of distilled water.

Example 2

Selective Adsorption of IgG

To test if the new non-aromatic sulphonamide ligands according to the invention adsorb human immunoglobulin (IgG) selectively, the adsorptivity of IgG and three different model proteins was been tested at various conditions. The principle of the test method was that proteins were injected (15 µl) into an HR5/5 column (containing the sulphonamide ligands immobilised on SEPHAROSE™ Fast Flow (GE Healthcare Bio-Sciences AB, Uppsala, Sweden) equilibrated with the A-buffer (containing a salt and a buffer component). Fifteen ml of A-buffer was then pumped through the column; then a 5-ml linear gradient from A-buffer to B-buffer (with B-buffer containing buffer component without salt) was applied (see UNICORN™ method below). The chromatographic profiles were then monitored at 280, 254 and 215 nm.

To evaluate the amount of sample adsorbed and amount of sample eluted from the column, the same amount of sample applied to the column was also injected directly to the monitor and the response was integrated.

Experimental

Six combinations of adsorption (Buffer A#) and desorption buffers (Buffer B#) were used:
1. Buffer A1: 20 mM phosphate buffer (pH 7.4) with 0.50 M $Na_2SO_4$ Buffer B1: 20 mM phosphate buffer (pH 7.4)
2. Buffer A2: 20 mM phosphate buffer (pH 7.4) with 0.25 M $Na_2SO_4$ Buffer B1: 20 mM phosphate buffer (pH 7.4)
3. Buffer A3: 20 mM acetate buffer (pH 4.0) with 0.50 M $Na_2SO_4$ Buffer B2: 20 mM acetate buffer (pH 4.0)
4. Buffer A4: 20 mM acetate buffer (pH 4.0) with 0.25 M $Na_2SO_4$ Buffer B2: 20 mM acetate buffer (pH 4.0)
5. Buffer A2: 20 mM phosphate buffer (pH 7.4) with 0.25 M $Na_2SO_4$ Buffer B3: 100 mM acetate buffer (pH 4.0)
6. Buffer A5: 20 mM Glycine buffer (pH 10.0) with 0.50 M $Na_2SO_4$ Buffer B4: 20 mM Glycine buffer Sample The samples used were bovine serum albumin (BSA), ribonuclease A (RIB A), transferrin (TRANSF) and human immunoglobulin (IgG, Gammanorm). The proteins were dissolved in the A-buffers at a concentration of 15 mg/ml and only one protein at a time was applied into the column.

Instrumental

| | Apparatus |
|---|---|
| | Liquid Chromatography |
| (LC) System: | ÄKTAEXPLORER ™ (GE Healthcare Bio-Sciences AB, Uppsala, Sweden)10 XT or equal |
| Software: | UNICORN ™ |
| Injection loop: | SUPERLOOP ™ 5 µl |
| Column: | HR 5/5 |
| | Instrument parameters |
| Flow rate: | 0.5 ml/min |
| Detector cell: | 10 mm |
| Wavelength: | 280, 254 and 215 nm |

UNICORN ™ method
Main method:

| | |
|---|---|
| 0.00 | Base CV, 1.00 {ml}, Any |
| 0.00 | Column Position Position1 Bypass |
| 0.00 | AutoZeroUV |
| 0.00 | Wavelength 280 {nm} 254 {nm} 215 {nm} |
| 1.00 | Wavelength 280 {nm} 254 {nm} 215 {nm} |
| 1.10 | InjectionPartial (1)#VIAL, 10#INJVOL1 {µl}, No, NoAir |
| 1.10 | AutoZeroUV |
| 4.00 | ColumnPosition (Position2)KOLONN |
| 5.00 | InjectionPartial (1)#VIAL2, 10#INJVO2 {µl}, No, NoAir |
| 20.00 | Gradient 100 {% B}, 2.00 {base} |
| 25.00 | Gradient 100 {% B}, 0.00 {base} |
| 25.10 | Gradient 0 {% B}, 1 {base} |
| 29.00 | Gradient 0 {% B}, 0 {base} |
| 34.00 | Gradient 0 {% B}, 0 {base} |
| 34.10 | End method |

Results and Discussion

1(a) Sulphonamide Ligands: Adsorption at pH 7.4 and Conditions for Desorption

To document if non-aromatic sulphonamide ligands selectively adsorb immunoglobulines, human IgG has been applied to a 1 ml column (HR 5/5) packed with the new matrices according to the invention. In addition, the proteins bovine serum albumin (BSA), ribonuclease A (RIB A) and transferrin (TRANSF) were also applied. Five different buffers with different pH and different content of salt ($Na_2SO_4$) were used as adsorption buffers. In Table 1 and 2, the results from pH 7.4 (Buffers A1 and A2) are presented. As appears from Table 1 below, when 0.25 M of $Na_2SO_4$ was added to the mobile phase, BSA, RIB A and TRANSF were not adsorbed to the ligands investigated. However, IgG was quantitatively adsorbed to three of the four ligands based on polyamines and 90% of the applied IgG was adsorbed to the fourth ligand, i.e. the ligand based on triethylenetetramine. Furthermore, only one of the ammonias (monamines), i.e. the ligand based on cysteamine, adsorbed IgG.

TABLE 1

Adsorbed amount of bovine serum albumin (BSA), ribonuclease A (RIB A), transferrin (TRANSF) or human immunoglobulin (IgG) on different sulphonamide ligands using 20 mM phosphate buffer (pH 7.4) with 0.25 M $Na_2SO_4$ (Buffer A2) as adsorption buffer.

| Sulphonamide ligands[a] | Relative adsorbed amount (%)[b] | | | |
|---|---|---|---|---|
| | BSA | RIB A | TRANSF | IgG |
| Cysteamine | 0 | 0 | 0 | 50 |
| Triethylene-tetramine | 0 | 0 | 0 | 90 |
| Diethylenetriamine | 0 | 0 | 0 | 100 |
| Pentaethylene-hexamine | 0 | 0 | 0 | 100 |
| Polyethyleneimine | 0 | 0 | 0 | 100 |
| Ammonia 1 | 0 | 0 | 0 | 0 |
| Ammonia 2 | 0 | 0 | 0 | 0 |

[a] The ligands have been converted to sulphonamide via reaction with $CH_3SO_2Cl$ (See the section for preparation of sulphonamide media).
[b] The relative adsorbed amount: ((Adsorbed amount/Applied amount) × 100). The adsorbed amount was calculated according to: (Applied amount – the amount eluted with the adsorption buffer)

As appears from Table 2 below, if a mobile phase with a higher ionic strength (Buffer A1; 0.50 M of $Na_2SO_4$) was used, transferrin was partly adsorbed to some of the ligands (Table 2) and IgG was adsorbed to all ligands. The most selective ligands were the sulphonamide ligands based on diethylenetriamine, polyethyleneimine and Ammonia 1 (Table 2) since BSA, RIB A and TRANSF were not adsorbed to these ligands.

TABLE 2

Adsorbed amount of bovine serum albumin (BSA), ribonuclease A (RIB A), transferrin (TRANSF) or human immunoglobulin (IgG) on different sulphonamide ligands using 20 mM phosphate buffer (pH 7.4) with 0.50 M $Na_2SO_4$ (Buffer A1) as adsorption buffer.

| Sulphonamide ligands[a] | Relative adsorbed amount (%)[b] | | | |
|---|---|---|---|---|
| | BSA | RIB A | TRANSF | IgG |
| Cysteamine | 10 | 5 | 5 | 95 |
| Triethylene-tetramine | 0 | 0 | 0 | 95 |
| Diethylenetriamine | 0 | 0 | 0 | 100 |
| Pentaethylenehexamine | 0 | 0 | 10 | 100 |
| Polyethyleneimine | 0 | 0 | 0 | 100 |
| Ammonia 1 | 0 | 0 | 0 | 100 |
| Ammonia 2 | 0 | 0 | 0 | 60 |

[a]The ligands have been converted to sulphonamide via reaction with $CH_3SO_2Cl$ (See the section for preparation of sulphonamide media).
[b]The relative adsorbed amount: ((Adsorbed amount/Applied amount) × 100). The adsorbed amount was calculated according to: (Applied amount − the amount eluted with the adsorption buffer)

The results presented above show that depending on the ion strength of the pH 7.4 adsorption buffer, different sulphonamide ligands will be optimal for IgG adsorption.

An ideal adsorbent for immunoglobulin must not only have a significant selectivity but should also be able to permit an efficient elution. Most of the adsorbed IgG could easily be desorbed with 20 mM phosphate buffer (pH 7.4) with no salt added. Adsorption of IgG using buffer A1 as mobile phase resulted in a recovery of 70-100% of the adsorbed IgG when desorption buffer B1 was used. However, IgG was more difficult to elute when adsorbed with buffer A2, but could easily be desorbed by using buffer B3 (100 mM acetate buffer, pH 4.0).

1(b): Sulphonamide Ligands: Adsorption at pH 4.0 and Conditions for Desorption

As appears from Table 3 and 4 below, adsorption of IgG at acidic conditions is clearly not as selective as adsorption at pH 7.4. By using 20 mM acetate buffer (pH 4.0) with addition of 0.25 M $Na_2SO_4$ (Buffer A4) as adsorption buffer, the ligands based on cysteamine, triethylenetetramine and diethylenetriamine adsorb 40, 40 and 60%, respectively, of the applied amount of IgG (Table 3). At the same conditions ribonuclease A and transferrin are not adsorbed. However, 90, 10 and 100% of applied bovine serum albumin are adsorbed to the ligands based on cysteamine, triethylenetetramine and diethylenetriamine, respectively.

TABLE 3

Adsorbed amount of bovine serum albumin (BSA), ribonuclease A (RIB A), transferrin (TRANSF) or human immunoglobulin (IgG) on different sulphonamide ligands using 20 mM acetate buffer (pH 4.0) with 0.25 M $Na_2SO_4$ (Buffer A4) as adsorption buffer.

| Sulphonamide ligands[a] | Relative adsorbed amount (%)[b] | | | |
|---|---|---|---|---|
| | BSA | RIB A | TRANSF | IgG |
| Cysteamine | 90 | 0 | 0 | 30 |
| Triethylene-tetramine | 10 | 0 | 0 | 30 |
| Diethylenetriamine | 100 | 0 | 0 | 60 |
| Pentaethylenehexamine | 0 | 0 | 0 | 10 |
| Polyethyleneimine | 0 | 0 | 0 | 0 |

TABLE 3-continued

Adsorbed amount of bovine serum albumin (BSA), ribonuclease A (RIB A), transferrin (TRANSF) or human immunoglobulin (IgG) on different sulphonamide ligands using 20 mM acetate buffer (pH 4.0) with 0.25 M $Na_2SO_4$ (Buffer A4) as adsorption buffer.

| Sulphonamide ligands[a] | Relative adsorbed amount (%)[b] | | | |
|---|---|---|---|---|
| | BSA | RIB A | TRANSF | IgG |
| Ammonia 1 | 20 | 0 | 0 | 0 |
| Ammonia 2 | na | na | na | 0 |

[a]The ligands have been converted to sulphonamide via reaction with $CH_3SO_2Cl$ (See the section for preparation of sulphonamide media).
[b]The relative adsorbed amount: ((Adsorbed amount/Applied amount) × 100). The adsorbed amount was calculated according to: (Applied amount − the amount eluted with the adsorption buffer)
na: Not analysed.

The results above show that the ligand based on triethylenetetramine is the most selective of the ligands tested for IgG. The sample IgG contains subclasses of different immunoglobulins (59% of IgG 1, 36% of IgG 2, 4.9% of IgG 3 and 0.5% of IgG 4). If the salt content in the adsorption buffer increases, the selectivity for IgG decreases as a result of adsorption of the other proteins. In Table 4 results are presented for buffer A3 (20 mM acetate buffer (pH 4.0) with 0.50 M $Na_2SO_4$) used as adsorption buffer. It is clearly shown that both ribonuclease A and transferrin are adsorbed to some of the ligands. Furthermore, bovine serum albumin is adsorbed to a higher degree with buffer A3 compared to when buffer A4 was used (Table 3 and 4). The ligand that is most selective when buffer A3 is used seems to be the one based on pentaethylenehexamine since only 10, 20 and 10% are adsorbed of applied amount of BSA RIB and TRANSF, respectively. This can be compared to IgG where 50% of the applied amount is adsorbed (Table 4).

TABLE 4

Adsorbed amount of bovine serum albumin (BSA), ribonuclease A (RIB A), transferrin (TRANSF) or human immunoglobulin (IgG) on different sulphonamide ligands using 20 mM acetate buffer (pH 4.0) with 0.5 M $Na_2SO_4$ (Buffer A3) as adsorption buffer.

| Sulphonamide ligands[a] | Relative adsorbed amount (%)[b] | | | |
|---|---|---|---|---|
| | BSA | RIB A | TRANSF | IgG |
| Cysteamine | 100 | 80 | 70 | 100 |
| Triethylene-tetramine | 50 | 80 | 45 | 70 |
| Diethylenetriamine | 100 | 100 | 0 | 100 |
| Pentaethylenehexamine | 10 | 20 | 10 | 50 |
| Polyethyleneimine | 0 | 40 | 0 | 10 |
| Ammonia 1 | 100 | 30 | 0 | 100 |
| Ammonia 2 | 10 | 40 | 0 | 20 |

[a]The ligands have been converted to sulphonamide via reaction with $CH_3SO_2Cl$ (See the section for preparation of sulphonamide media).
[b]The relative adsorbed amount: ((Adsorbed amount/Applied amount) × 100). The adsorbed amount was calculated according to: (Applied amount − the amount eluted with the adsorption buffer)

Quantitative desorption of all adsorbed samples was easily accomplished by buffer B2 (20 mM acetate buffer, pH 4.0).

1(c): Sulphonamide Ligands: Adsorption at pH 10.0 and Conditions for Desorption

A few experiments have been conducted at pH 10.0, and according to Table 5 it can be seen that IgG is quantitatively adsorbed to the ligands based on cysteamine and triethylenetetramine by using adsorption buffer A5 (20 mM Glycine buffer (pH 10.0) with 0.5 M $Na_2SO_4$). However, only 10% of the adsorbed amount of IgG could be eluted with desorption buffer B4 (20 mM Glycine buffer). To obtain quantitative desorption of IgG the pH has to be changed to acidic conditions, for example by using desorption buffer B3 (100 mM acetate buffer, pH 4.0).

TABLE 5

Adsorbed amount human immunoglobulin (IgG) on two different sulphonamide ligands using 20 mM acetate buffer (pH 4.0) with 0.50 M $Na_2SO_4$ (Buffer A3), 20 mM phosphate buffer (pH 7.4) with 0.50 M $Na_2SO_4$ (Buffer A1) or 20 mM Glycine buffer (pH 10.0) with 0.5 M $Na_2SO_4$ (Buffer A5) as adsorption buffers.

| Sulphonamide ligands[a] | Relative adsorbed amount of IgG (%)[b] | | |
|---|---|---|---|
| | pH 4.0 | pH 7.4 | pH 10.0 |
| Cysteamine | 100 | 95 | 100 |
| Triethylene-tetramine | 70 | 95 | 100 |

[a]The ligands have been converted to sulphonamide via reaction with $CH_3SO_2Cl$ (See the section for preparation of sulphonamide media).
[b]The relative adsorbed amount: ((Adsorbed amount/Applied amount) × 100). The adsorbed amount was calculated according to: (Applied amount − the amount eluted with the adsorption buffer)

Example 3

Comparison Between $CH_3SO_2Cl$ and $CH_3COCl$ Modified Amine Ligands (Methylsulphonamide and Acetamide Ligands)

In order to verify that sulphonamide structures according to the invention interact with antibodies more strongly than acetamide ligands, two ligands of each type were prepared based on the two amine ligands triethylentetramine and cysteamine (according to example 2, experimental section, above). In Table 6 below, the results of IgG adsorption for four different buffer systems (Buffers B1-3 and B5) are presented. As appears clearly from Table 6, the sulphonamide structures according to the invention adsorb IgG more effectively at all investigated conditions compared to the acetamide ligands. The acetamide ligand based on cysteamine was the only ligand that could adsorb IgG (50% of the amount applied) when buffers A1 and A5 were used as adsorption buffers. However, this ligand was unable to adsorb IgG when the salt concentration decreased from 0.5 M to 0.25 M $Na_2SO_4$ in 20 mM phosphate buffer (pH 7.4). Both methylsulphonamide ligands adsorb IgG at all investigated conditions. These results clearly indicate that methylsulphonamide ligands according to the invention are better IgG adsorbers than acetamide-ligands.

TABLE 6

Adsorbed amount of human immunoglobulin (IgG) on sulphonamide and acetamide ligands at four different adsorption buffers.

| Ligands | Relative adsorbed amount of IgG (%) | | | |
|---|---|---|---|---|
| | Buffer A1[a] | Buffer A2[b] | Buffer A3[c] | Buffer A5[d] |
| Methylsulphonamide derivative[e] of triethylentetramine | 95 | 90 | 100 | 100 |
| Methylsulphonamide derivative[e] of cysteamine | 95 | 50 | 70 | 100 |
| Acetamide derivative[f] of triethylenetetramine | 0 | 0 | 0 | 0 |
| Acetamide derivative[f] of cysteamine | 50 | 0 | 0 | 50 |

[a]Buffer A1: 20 mM phosphate buffer (pH 7.4) with 0.50 M $Na_2SO_4$
[b]Buffer A2: 20 mM phosphate buffer (pH 7.4) with 0.25 M $Na_2SO_4$
[c]Buffer A3: 20 mM acetate buffer (pH 4.0) with 0.50 M $Na_2SO_4$
[d]Buffer A5: 20 mM Glycine buffer (pH 10.0) with 0.50 M $Na_2SO_4$
[e]The ligand has been converted to sulphonamide via reaction with $CH_3SO_2Cl$ (See the section for preparation of sulphonamide media).
[f]The ligand has been converted to amide via reaction with $CH_3COCl$ (See the section for preparation The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of isolating antibodies from a liquid, which method comprises the steps of:
    (a) providing a liquid that comprises at least one antibody;
    (b) contacting said liquid with a separation matrix, which comprises one or more aliphatic sulphonamide ligands, to adsorb one or more antibodies to said matrix;
    (c) passing an eluent over said matrix to release one or more antibodies; and
    (d) recovering at least one antibody from a fraction of the eluent.

2. The method of claim 1, wherein the liquid provided in step (a) additionally comprises one or more other proteins.

3. The method of claim 1, wherein the separation matrix of step (b) is provided in a chromatography column.

4. The method of claim 3, wherein step (b) is performed at a close to neutral pH.

5. The method of claim 1, wherein the separation matrix of step (b) comprises a porous support; and ligands including one or more sulphonamides wherein an R group of the sulphonyl is an aliphatic compound; wherein said ligands are immobilized, optionally via spacer arms, on said porous support.

6. The method of claim 1, wherein step (c) is a gradient elution performed by adding an eluent of decreasing salt concentration to the separation matrix.

7. The method of claim 1, wherein step (b) is performed at a pH of or above neutral and step (c) is a gradient elution performed by adding an eluent of decreasing pH.

8. The method of claim 1, wherein the antibodies recovered in step (d) are human or humanised antibodies.

9. The method of claim 1, wherein the antibodies recovered in step (d) are immunoglobulin G (IgG).

10. The method of claim 1, further comprising determining the amount of isolated antibody spectrophotometrically.

* * * * *